US010188871B2

(12) United States Patent
Simons et al.

(10) Patent No.: US 10,188,871 B2
(45) Date of Patent: Jan. 29, 2019

(54) FLAT OPTOGENETIC CUFF INTERFACE (FOCI) FOR A SINGLE NERVE FASCICLE OF THE PERIPHERAL NERVOUS SYSTEM

(71) Applicant: Teledyne Scientific & Imaging, LLC, Thousand Oaks, CA (US)

(72) Inventors: Stephen Simons, Raleigh, NC (US); Jiangying Zhou, Durham, NC (US); Mark A. Peot, Chapel Hill, NC (US); Warren Grill, Chapel Hill, NC (US); Dennis Turner, Cary, NC (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 892 days.

(21) Appl. No.: 14/668,523

(22) Filed: Mar. 25, 2015

(65) Prior Publication Data

US 2016/0279438 A1    Sep. 29, 2016

(51) Int. Cl.
*A61N 5/06*    (2006.01)

(52) U.S. Cl.
CPC ......... *A61N 5/0601* (2013.01); *A61N 5/0622* (2013.01); *A61N 2005/0626* (2013.01)

(58) Field of Classification Search
CPC .............................. A61N 5/062; A61B 8/0057
USPC ..................................................... 606/86–94
See application file for complete search history.

(56) References Cited

U.S. PATENT DOCUMENTS

| | | |
|---|---|---|
| 6,456,866 B1 | 9/2002 | Tyler et al. |
| 8,868,211 B2 | 10/2014 | Durand et al. |
| 2008/0046055 A1* | 2/2008 | Durand ................ A61N 1/0556 607/118 |
| 2009/0093403 A1* | 4/2009 | Zhang ................ A01K 67/0333 514/8.1 |

(Continued)

OTHER PUBLICATIONS

Arlow et al. Theoretical Principles Underlying Optical Stimulation of Myelinated Axons Expressing ChannelRhodopsin-2, Neuroscience, Sep. 17, 2013.*

(Continued)

*Primary Examiner* — Carl H Layno
*Assistant Examiner* — Dacheng Xie
(74) *Attorney, Agent, or Firm* — Eric A. Gifford

(57) ABSTRACT

A flat optogenetic cuff interface (FOCI) is configured for functional optical stimulation of axons in a single fascicle of a peripheral nerve bundle in which the axons have been genetically modified to express light sensitive proteins for excitation or inhibition of the nerves. The FOCI is configured to gradually reshape the single fascicle to a final height between 0.2 mm and 0.5 mm by reorganizing the individual axons within the fascicle without reshaping (and damaging) the individual axons. The FOCI facilitates stimulation of axons over the entire cross-section of the reshaped fascicle within the power limitations for pulsed laser energy. An electrical interface may be included to sense nerve activity of either the stimulated axons to provide closed-loop feedback to control the optical sources or stimulated axons of a different modality to record the response. The FOCI may be used as an interface for prosthetic devices to restore lost sensory or motor function, to augment human sensor or motor performance or to modulate autonomic functions.

14 Claims, 7 Drawing Sheets

(56) References Cited

U.S. PATENT DOCUMENTS

2012/0253261 A1* 10/2012 Poletto .............. A61M 5/14276
604/20
2013/0184636 A1* 7/2013 Creasey ................ A61N 5/062
604/20

OTHER PUBLICATIONS

Llewellyn et al., Orderly Recruitment of MOtor Units Under Optical Control In Vivo, Nat Med, Sep. 26, 2010).*
Rohm, SMLP12BC7T datasheet, 2007.*
Edward S. Boyden, "A history of optogenetics: the development of tools for controlling brain circuits with light," F1000 Reports Biology, published May 3, 2011, pp. 1-12.
Caparso et al., "Nerve Cuff Electrode for Controlled Reshaping of Nerve Geometry," Journal of Biomaterials Applications, vol. 24, Sep. 2009, pp. 247-273.
Fenno et al., "The Development and Application of Optogenetics," Annual Review of Neuroscience. 2011, pp. 389-412.
Warden et al., Optical Neural Interfaces, Annu Rev Biomed Eng. Jul. 11, 2014; 16: 103-129.
Towne et al., "Optogenetic Control of Targeted Peripheral Axons in Freely Moving Animals," PLOS One, Aug. 2013, vol. 8, Issue 8, pp. 1-10.

* cited by examiner

BUNDLED-FASCICLE FOCI

SINGLE-FASCICLE FOCI

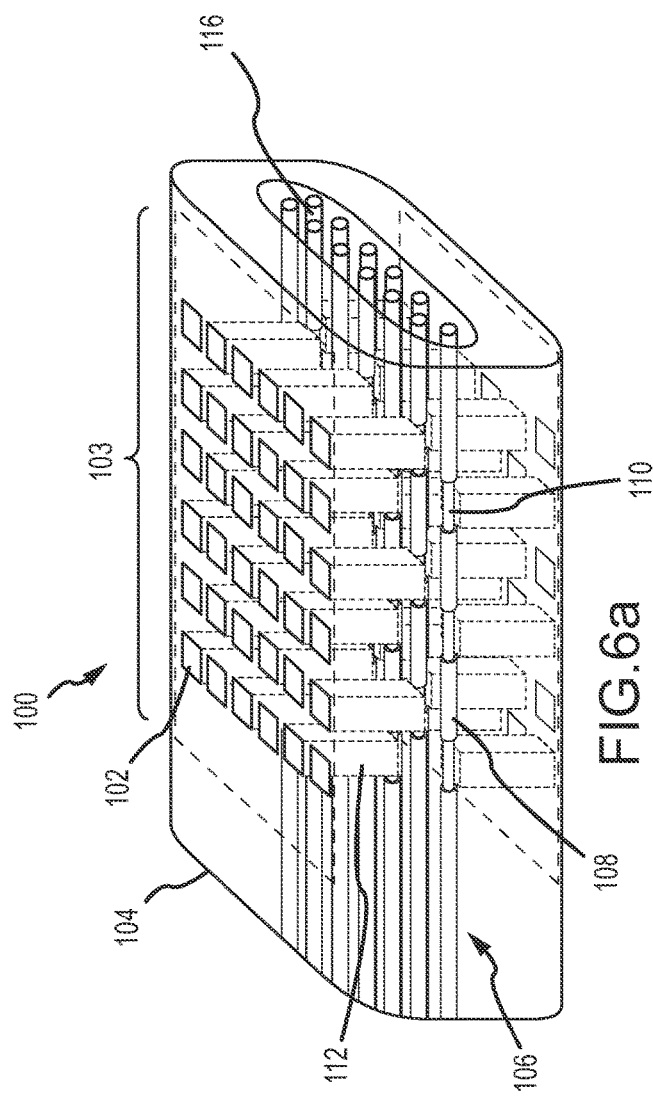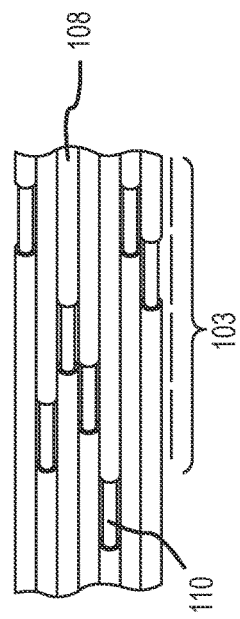

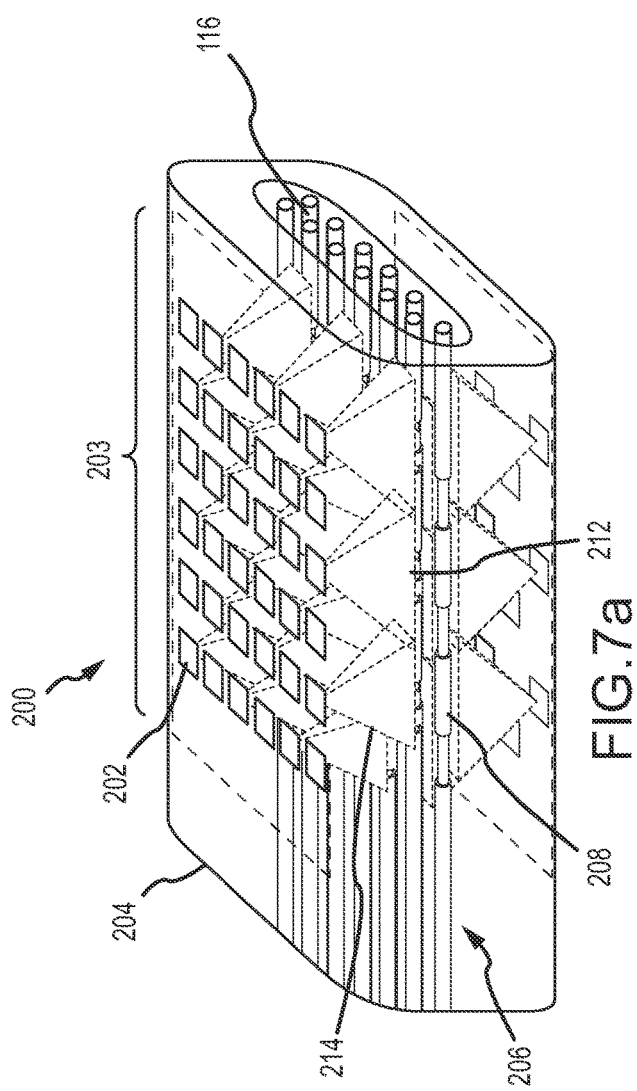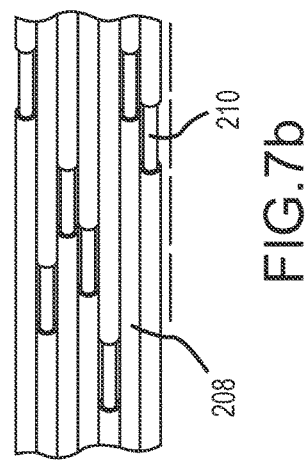

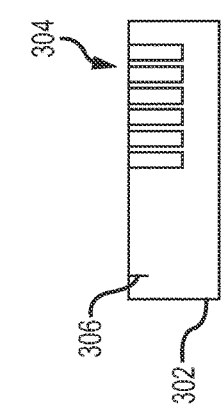
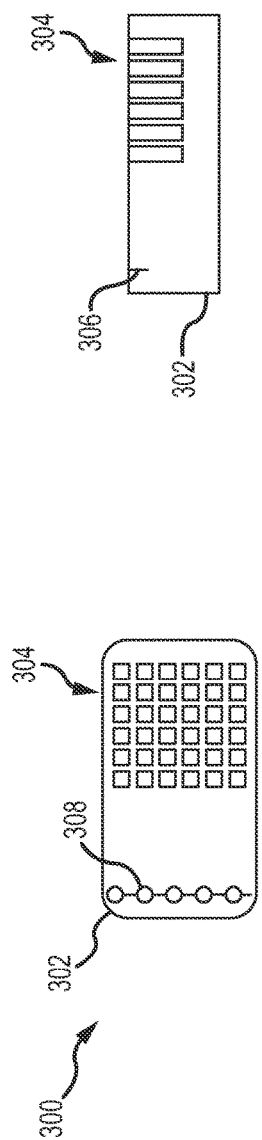
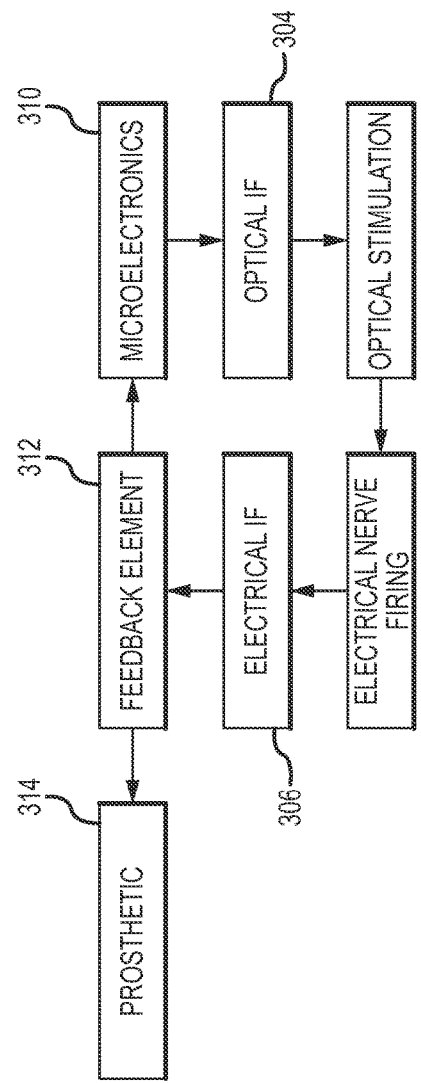

FLAT OPTOGENETIC CUFF INTERFACE (FOCI) FOR A SINGLE NERVE FASCICLE OF THE PERIPHERAL NERVOUS SYSTEM

BACKGROUND OF THE INVENTION

Field of the Invention

This invention relates to implantable biomedical interfaces for the peripheral nervous system, and more particularly to a cuff for biologic soft tissue that can be used to optically stimulate axons in a single fascicle without damaging the nerves.

Description of the Related Art

The peripheral nervous system (PNS) consists of the nerves outside of the brain and spinal cord. The main function of the PNS is to connect the central nervous system (CNS) to the limbs and organs, serving as a communication relay between the brain and the extremities. The PNS includes motor nerves for motor control, sensor nerves for sensory functions such as touch, temperature, pressure, vibration and shear and autonomic nerves for such functions as controlling heart rate, digestion, immune system, flight or fight, etc. A peripheral nerve bundle for a particular function (sensory, motor, autonomic) includes multiple fascicles for different regions of the body with each fascicle including multiple axons (e.g. 10,000 to 100,000) for different functional sub-modalities (e.g. touch, temperature, pressure, etc.). The peripheral nerve bundle will branch out as it extends to the extremities, possibly to a single fascicle.

Biomedical devices and therapies are evolving that target the precise application of stimuli to specific nerve modalities and sub-modalities and recording of the effects of their stimulation. Such devices and therapies may be used as an interface for prosthetic devices to restore lost sensory or motor function, to augment human sensory or motor performance or to modulate autonomic functions.

Cuff electrodes have been used to provide a neural interface for direct electrical stimulation of peripheral nerves. One type of cuff is a soft tissue cuff that is placed around the peripheral nerve bundle and is non-invasive to the soft tissue.

U.S. Pat. No. 6,456,866 entitled "Flat Interface nerve electrode and a method for use" and referred to as FINE discloses a plurality of conductive elements embedded in a non-conductive cuff structure, which acts to gently redefine the geometry of a nerve through the application of a force so as to apply pressure to a nerve. The cuff has an opening, which is elongated relative to the diameter of the nerve to which it is applied. Preferably, the cuff is constructed from an elastic biocompatible material having top and bottom beam members configured to define a nerve opening. The cuff is open at one side and has a connection at the other side, which results in a spring force being applied through the surfaces of the nerve opening to the subject nerve. During implantation the open sides of the cuff are closed so as to capture the nerve in the cuff. As the nerve is reshaped, specific nerve axons become more easily addressed through the epineurium by the embedded conductive elements. Flattening the nerve provides selectivity, i.e. the ability to activate and record a specific population or subset of axons within a nerve.

Anthony V. Caparso et. al. developed a variant on the FINE know as the Slowly Closing—FINE or SC-FINE as described in "A nerve cuff electrode for controlled reshaping of nerve geometry" Journal Of Biomaterials Applications Volume 24—September 2009 pp. 247-273. The SC-FINE provides more precise control over the rate of closure and the gradual reshaping of the peripheral nerve bundle. The SC-FINE combines the reshaping properties of the FINE and the controllable degradation of poly DL lactic-co-glycolic acid (PLGA). A PLGA film is bonded to a stretched FINE. As the film degrades in-situ, the FINE returns to its original geometry and gradually reshapes the peripheral nerve bundle.

Optogenetics is a neuromodulation technique that combines techniques from optics and genetics to control and monitor the activities of individual neurons in living tissues. Axons corresponding to a particular modality or sub-modality are genetically modified to express light sensitive proteins for excitation or inhibition of the nerves when stimulated with light of a particular wavelength. See Lief Fenno et al. "The Development and Application of Optogenetics" Annua. Rev. Neurosci. 2011 34: 389-412. Unlike electrical stimulation, which will stimulate any and all nerves proximate to the electrode (hence the FINE and SC-FINE cuffs that flatten the nerve bundle), optogenetic stimulation can be targeted to a particular modality or sub-modality to provide the selectivity to interface with specific populations or subsets of axons within a nerve.

Chris Towne et. al. "Optogenetic Control of Targeted Peripheral Axons in Freely Moving Animals" PLOS ONE, August 2013 Volume 8, Issue 8 reports on methods to deliver opsins and light to targeted peripheral neurons for robust optogenetic modulation of motor neuron activity. As shown in FIG. 3, a biocompatible spiral cuff constructed from polydimethylsilloxane (PDMS) covalently bonded to a silicon-based optical fiber and terminated with a stainless steel ferrule were implanted into rats around the sciatic nerve. Light pulsed at 36 Hz with a pulse width of 5 ms and a power level of 20 mW was used to stimulate motor nerves in rats walking on a treadmill.

SUMMARY OF THE INVENTION

The following is a summary of the invention in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description and the defining claims that are presented later.

The present invention provides a flat optogenetic cuff interface (FOCI) for functional optical stimulation of axons in a single fascicle of a peripheral nerve bundle in which the axons have been genetically modified to express light sensitive proteins for excitation or inhibition of the nerves. The FOCI is configured to gradually reshape the single fascicle to a final height between 0.2 mm and 0.5 mm by reorganizing the individual axons within the fascicle without reshaping (and damaging) the individual axons. The FOCI facilitates stimulation of axons over the entire cross-section of the reshaped fascicle within the power limitations (i.e. Maximum Permissible Exposure) for pulsed laser energy dictated by safety concerns and regulations. The FOCI also enhances the specificity with which axons in the fascicle can be addressed.

In an embodiment, a FOCI comprises a cuff configured for a single nerve fascicle having an external configuration with a height Y and a width X. The cuff comprises an elastic collar member defining an internal opening which has an internal configuration having a height less than Y and between 0.2 mm and 0.5 mm and a width greater than X. The collar member includes a material that exerts a force on said nerve fascicle that will cause the fascicle to gradually reshape to the internal configuration of said opening, the gradual reshaping of the fascicle reorganizing the axons within the fascicle without reshaping the individual axons. An optical interface comprises a plurality of optical sources arranged in a two-dimensional array on the cuff, either a single two-dimensional array on one side of the cuff or a pair of two-dimensional arrays on opposing sides of the cuff. The optical interface may be formed on an interior surface of the elastic collar member or embedded within an optically transparent elastic collar member. The optical sources are configured to emit pulsed light to penetrate the reshaped nerve fascicle from one or opposing sides to stimulate axons over an entire cross-section of the reshaped nerve fascicle along a length of the nerve of at least 2 mm.

In different embodiments, the cuff may comprise a FINE or SC-FINE cuff formed of optically transparent materials.

In different embodiments, the optical sources emit pulsed light at a pulse repetition frequency up to 40 Hz and power level such that the irradiance incident upon tissue is less than a Maximum Permissible Exposure (MPE) and the irradiance incident at the center of the cross-section is greater than a Minimum Source Power (MSP) to stimulate axons, wherein the MPE is the minimum of a single pulse limit, an average power limit and repetitive pulse limit. The activation of a single one of the optical sources illuminates a length of the nerve of at least 50 microns and less than 10% of the cross-section of the reshaped nerve fascicle. In another embodiment, the PRF is up to 100 Hz.

In different embodiments, the FOCI further comprises an electrical interface. The electrical interface comprises a plurality of electrodes across the width of the cuff configured to sense activity of axons within the fascicle. In an embodiment, the electrical interface is used to sense and record activity of a different functional modality than the optically stimulated axons. In another embodiment, the electrical interface is used to sense the activity of the optically stimulated axons and feedback that activity to control the optical sources. In another embodiment, the electrical interface is used to provide closed-loop feedback to control the optical sources and to record activity of a different functional modality.

In different embodiments, the optical interface may be configured to provide either single wavelength of a single modality or sub-modality or multi-wavelength stimulation of different sub-modalities. For multi-wavelength stimulation, the optical interface may be configured to emit pulsed light in either overlapping or non-overlapping fields of view (FOV) within the reshaped fascicle, and the optical sources may be configured to emit pulsed light at fixed wavelengths or selectable wavelengths.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 6a and 6b are diagrams of an optical interface for single or multi-wavelength stimulation of the axons in the single fascicle using collimated light;

FIGS. 7a and 7b are diagrams of an optical interface for multi-wavelength stimulation of the axons in the single fascicle using uncollimated light; and FIGS. 8a, 8b and 8c are plan and sides and a block illustrating an electrical interface for recording axon activation for closed-loop feedback for the optical interface or bi-directional sensing.

DETAILED DESCRIPTION OF THE INVENTION

The present invention describes a flat optogenetic cuff interface (FOCI) for functional optical stimulation of axons in a single fascicle of a peripheral nerve bundle in which the axons have been genetically modified to express light sensitive proteins for excitation or inhibition of the nerves. The FOCI is configured to gradually reshape the single fascicle to a final height between 0.2 mm and 0.5 mm by reorganizing the individual axons within the fascicle without reshaping (and damaging) the individual axons. The FOCI facilitates stimulation of axons over the entire cross-section of the reshaped fascicle within the power limitations (i.e. Maximum Permissible Exposure) for pulsed laser energy dictated by safety concerns and regulations. The FOCI also enhances the specificity with which axons in the fascicle can be addressed. The optical interface may be configured to stimulate multiple functional sub-modalities. An electrical interface may be included to sense nerve activity of either the stimulated axons to provide closed-loop feedback to control the optical sources or stimulated axons of a different modality to record the response. The FOCI may be used as an interface for prosthetic devices to restore lost sensory or motor function, to augment human sensor or motor performance or to modulate autonomic functions.

Figure 1:
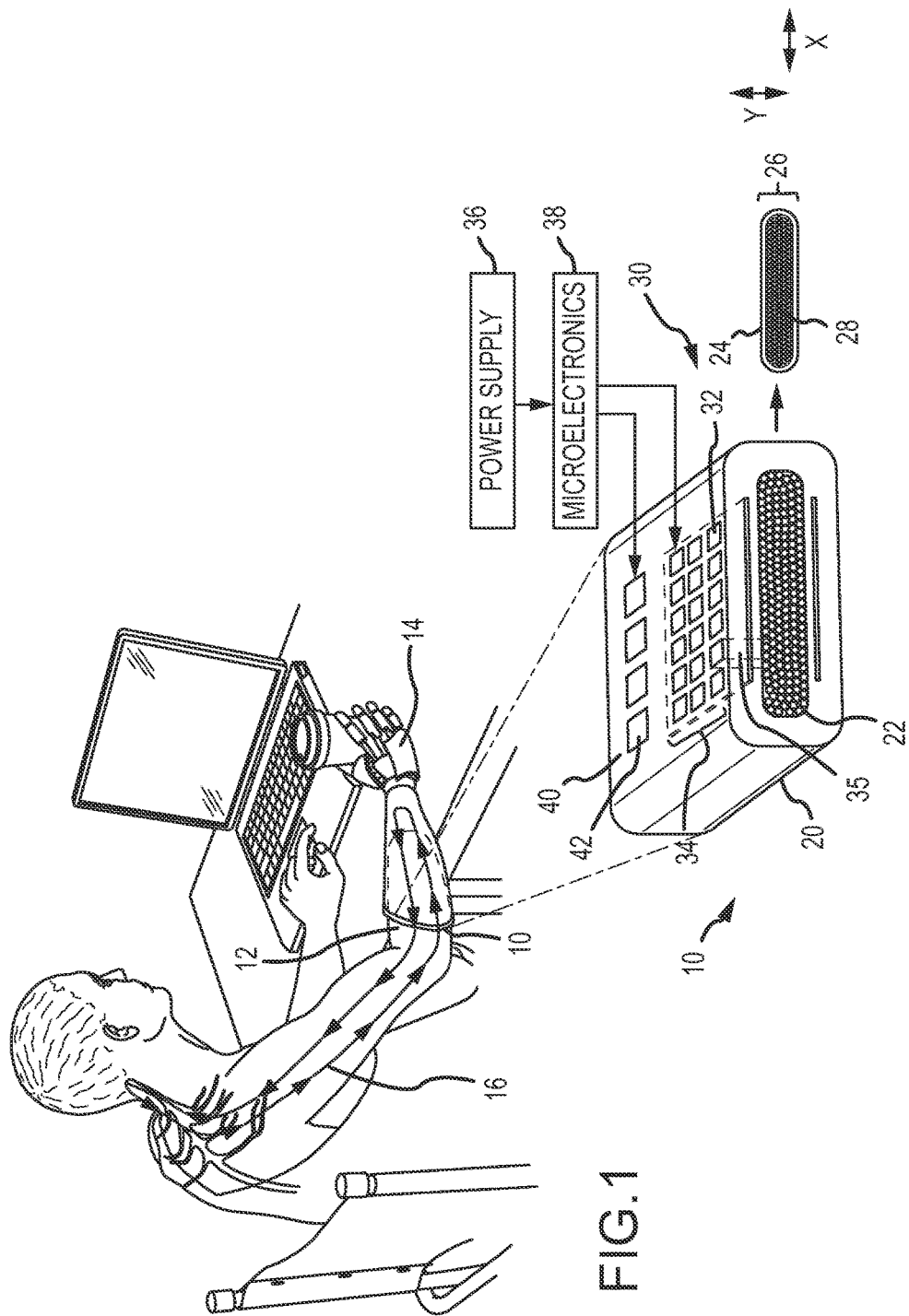
FIG. 1 is a diagram of a flat optical cuff interface (FOCI) implanted to provide an interface between a prosthetic hand and the peripheral nervous system.

Referring now to FIG. 1, in an embodiment a flat optical cuff interface (FOCI) 10 is implanted in a person's forearm 12 to provide an interface between a prosthetic hand 14 and the peripheral nervous system 16. Prosthetic hand 14 may include one or more sensors for touch, temperature, vibration, sheer etc. that generate sensory signals that are provided to FOCI 10 to stimulate the corresponding genetically modified axons in sensory nerves. Prosthetic hand 14 may also include one or more motor controllers that receive motor control signals from the FOCI 10 in response to stimulated motor nerves. Multiple FOCI implants may be required to provide an interface for different sensory sub-modalities and to cover different regions of the hand.

FOCI 10 includes a cuff 20 configured for a single nerve fascicle 22 having an external configuration with a height Y and a width X. The cuff 20 comprises an optically transparent elastic collar member 24 defining an internal opening 26 which has an internal configuration having a height Y' less than Y and between 0.2 mm and 0.5 mm and a width X' greater than X. The collar member 24 includes a material (e.g. silicone elastomer) that exerts a force on the nerve fascicle 22 that will cause the fascicle to gradually reshape to the internal configuration of opening 26. The gradual reshaping of the fascicle reorganizes axons 28 within the fascicle without reshaping (and damaging) the individual axons. A silicone elastomer material provides an optically transparent elastic collar member.

An optical interface 30 is embedded within the optically transparent elastic collar member 24. The interface comprises a plurality of optical sources 32 (e.g. LEDs) arranged in two-dimensional arrays 34 on opposing sides of the cuff. For example, an LED array can be formed on a flexible substrate and inserted into the cuff on either side of the fascicle. Alternately, the LED array could be inserted on only one side of the cuff. The optical sources are configured to emit pulsed light 35 to penetrate the reshaped nerve fascicle 22 from opposing sides to stimulate axons 28 over an entire cross-section of the reshaped nerve fascicle along a length of the nerve of at least 2 mm. The activation of a single one of the optical sources illuminates a length of the nerve of at least 50 microns (the size of a Node of Ranvier) and preferably less than 10% or even 5% of the cross-section of the reshaped nerve fascicle.

In different embodiments, the optical interface may be configured to provide either single wavelength of a single modality or sub-modality or multi-wavelength stimulation of different sub-modalities. For multi-wavelength stimulation, the optical interface may be configured to emit pulsed light in either overlapping or non-overlapping fields of view (FOV) within the reshaped fascicle, and the optical sources may be configured to emit pulsed light at fixed wavelengths or selectable wavelengths.

A power supply 36 and microelectronics 38 are required to power the FOCI cuff and to provide control logic to the optical interface. Either or both component may be incorporated into the FOCI 10 or implanted elsewhere in the body and electrically connected to the FOCI. The power supply could be wireless in which case a transducer is incorporated into the cuff.

The power level of the optical sources is controlled such that the irradiance incident upon tissue is less than a Maximum Permissible Exposure (MPE) and the irradiance incident at the center of the cross-section is greater than a Minimum Source Power (MSP) to stimulate axons. The MPE is the minimum of a single pulse limit, an average power limit and repetitive pulse limit. In most applications, particularly for sensory nerves, the pulse repetition frequency may be up to 40 Hz. In subsets of peripheral sensory nerves the naturally occurring firing rate may be upwards of 100 Hz. The average power limit, which typically sets the MPE, is a function of the pulse repetition frequency, the higher the frequency the lower the MPE per pulse. Therefore it is critical that the final height of the reshaped fascicle is no greater than 0.5 mm in order to stay within the MPE and satisfy the MSP to stimulate axons.

In this embodiment, the FOCI 10 also includes an electrical interface 40 embedded within the elastic collar 24. The electrical interface comprises a plurality of electrodes 42 across the width of the cuff configured to sense activity of axons 28 within the fascicle 22. In an embodiment, the electrical interface is used to sense and record activity of a different functional modality (e.g. motor nerves) than the optically stimulated sensory axons. In another embodiment, the electrical interface is used to sense the activity of the optically stimulated sensory axons and feedback that activity to control the optical sources. This may be done to calibrate or maintain calibration of the optical sources to provide uniform stimulus. In another embodiment, the electrical interface is used to provide the closed-loop feedback to control the optical sources and to record activity of a different functional modality. The relative timing of sensed electrical signals relative to the optical stimulation will indicate whether the signals are those of the stimulated sensory nerves or stimulated motor nerves.

Optogenetics offers several potential advantages over electrical stimulation. First, stimulation of a particular functional modality can be isolated (e.g., vibration driven by rapidly adapting type-2 neurons, pressure driven by slowly adapting type-1 neurons). The axons corresponding to the particular functional modality are genetically modified to express light sensitive proteins for excitation or inhibition of the nerves at particular wavelength. This also provides potential advantages for bi-directional stimulation and recording. Second, multiple functional modalities can be simultaneously stimulated and maintain isolation from each other. The different functional modalities are genetically modified to express light sensitive proteins at different wavelengths e.g. opsins TsChR (410 nm), Chronos (500 nm) and ChrimsonR (625 nm). Third, the spatial resolution of the optical sources e.g. LEDs can be much higher due to the smaller footprint of the optical source compared to the electrode.

However, optogenetics also has a number of disadvantages over electrical stimulation. First and foremost are the power requirements to stimulate axons at the center of the nerve and constraints on the power levels to avoid nerve damage. The power level of the optical sources must be controlled such that the irradiance incident upon tissue is less than the Maximum Permissible Exposure (MPE) and the irradiance incident at the center of the cross-section is greater than the Minimum Source Power (MSP) to stimulate axons. Second, the varying depth of the axons produces a non-uniform stimulative effect for a given input power level. Third, the genetically modified axons can only be stimulated at "Nodes of Ranvier" that occur approximately every 1.5-2 mm at random locations.

For optogenetics to be viable beyond the research stage, the FOCI must provide a cuff and optical interface that is capable of exploiting the potential advantages and overcoming the disadvantages. At a first order, the FOCI must overcome the power limitations and exploit the inherent resolution advantages of optical sources for at least a single wavelength of stimulation. Preferred configurations of the FOCI may also provide for multi-wavelength stimulation, closed-loop feedback to provide uniform stimulation and bi-directional stimulation and recording.

Light Transport Modeling

Activation of genetically-sensitized nerve cells requires sufficient light intensity in the range of 1 $mW/mm^2$ to 0.1 $mW/mm^2$, dependent on the light-sensitive protein (opsin) used and their activation kinetics. Biological tissues absorb and scatter light. In order for the light to reach individual nerve fibers deep inside a nerve bundle, the energy level of the light source must be higher than the minimum required for optogenetic activation.

A Monte-Carlo simulation based on a light transport theory, which simulates absorption and scattering of coherent light in complex 3D tissue structures by simulating individual pixels as they are launched into the simulation space, was used to model the power requirement for the light source. The primary output of the Monte-Carlo simulation is the relative fluence rate $F(x,y,z)$ in $W/cm^2$ per W delivered at the optical input.

To study the light transport within a fascicle we used a simplified fascicle model as the model representative of a peripheral nerve fascicle. The specific choices of the model parameters are informed by historic studies published in the literature. According to these studies the diameter of human peripheral nerve fascicles ranges from 100 μm to 1000 μm.

Further, the perineurium thickness of human fascicles was found to be 3.0%±1.0% of the fascicle diameter. The selected model configuration, with a diameter of 800 µm, therefore, represents a close to the upper limit in the diameter distribution for peripheral nerves.

Light transport inside a fascicle is dependent on the spectrum of the light source and the optical properties of the tissues such as scattering and absorption. Accurate measurements of the optical properties of various tissues of the peripheral nerves (epineurium, perineurium, nerve fibers and endoneurium) are not currently available. We used measurements of other related tissue types as surrogate in this study. Table 1 summarizes the optical parameters (absorption $\mu_a$, scattering $\mu_s$, and anisotropy coefficient g of nerve tissues) used in our simulation.

TABLE 1

| | Optical properties at 540 nm | | |
|---|---|---|---|
| Optical Property | Epineurium | Perineurium | Nerve Fiber & Endoneurium |
| $\mu_a$ (cm$^{-1}$) | 1.2 | 1.2 | 1.0 |
| $\mu_s$ (cm$^{-1}$) | 82.2 | 82.2 | 426 |
| G | 0.785 | 0.785 | 0.81 |

In addition to the circular cross section fascicle model we also studied the light transport in a rectangular cross section fascicle model. In this model, we assume that the natural oval/circular shaped fascicle is reshaped by nerve compression to form a flattened rectangular cross section. We assume that the flattened fascicle cross section preserves the area of the original circular cross section, in other words:

$$W \times H = \pi \left(\frac{D}{2}\right)^2$$

Where W, H are the width and thickness of fascicle rectangular cross section, D is the diameter.

Thermal Analysis

For this analysis, we pursued three independent approaches for determining the increase in temperature due to absorption of the light pulse in the tissue inside and surrounding the fascicle. Approaches pursued:
1. Equilibrium: We determined the increase in temperature to very long exposures by convolving a time-independent Green's function with the calculated absorption in the thermal model.
2. Time-Dependent: We calculated the peak temperature rise after a sequence of light pulses by integrating the time-dependent Green's function.
3. Commercial: We confirmed our solution using a commercial multi-physics package, ANSYS Fluent (ANSYS Fluent) which also incorporates a model for heat dissipation in biological tissue.

Equilibrium Analysis: The heat equation is $$c\rho \frac{\partial u}{\partial t} = \nabla_x \cdot k \nabla_x u + Q$$

where k is the thermal conductivity, u is temperature, c is the heat capacity, ρ is the material density and Q is the thermal heat density (flux per unit volume) due to light that is absorbed throughout the volume.

TABLE 2

| Tissue | Thermal Conductivity (W/m/° C.) | |
|---|---|---|
| Name | Average | Standard Deviation |
| Blood | 0.52 | 0.03 |
| Blood Vessel Wall | 0.46 | 0.02 |
| Brain (White Matter) | 0.48 | 0.03 |
| Cartilage | 0.49 | 0.03 |
| Connective Tissue | 0.39 | 0.00 |
| Dura | 0.44 | 0.00 |
| Nerve | 0.49 | |

As can be seen from Table 2, the thermal conductivity of the tissues surrounding the nerve are roughly constant, allowing us to replace $\nabla_x \cdot k \nabla_x u$ with the Laplacian $k \nabla_x^2 u$.

When the temperature has reached an equilibrium, $$\frac{\partial u}{\partial t} = 0,$$

allowing us to write the stationary heat equation is $k \nabla_x^2 u = -Q$. The optical model calculates A, the optical absorption per unit volume per watt of applied power. Thus, the stationary heat equation we used was:

$$k \nabla^2 u = -A \overline{p}$$

where $\overline{p}$ is the average illumination power.

We solve for the equilibrium temperature of the surrounding tissue using the time-independent Green's function solution of $\nabla^2 u(x) = \delta(x)$, which is $$G(x; x') = -\frac{1}{4\pi |x - x'|}.$$

The equilibrium temperature is then given by the convolution $$u(x) = u_{body} + \frac{\overline{p}}{4\pi k} \int_{x'} \frac{A(x')}{|x - x'|} dx'.$$

We calculate this convolution directly using the light absorption, A, calculated by the Monte-Carlo simulation.

Time-Dependent Analysis: Assuming constant thermal conductivity, the inhomogeneous time-dependent heat equation is $$c\rho \frac{\partial u}{\partial t} = k \nabla^2 u + Q(x, t)$$

or $$\left(\frac{\partial}{\partial t} - \alpha \nabla^2\right) u = \frac{Q(x, t)}{c\rho}$$

where $\alpha = \frac{k}{c\rho}$.

The solution to $$\left(\frac{\partial}{\partial t} - \alpha \nabla^2\right) u = \delta(x, t) \text{ is}$$

$$\Phi(x, t) = (4\pi \alpha t)^{-3/2} \exp\left(\frac{-|x|^2}{4\alpha t}\right)$$

Using the optical absorption, Q=A(x)p(t), the general solution to the heat equation is then $$u(x, t) = \frac{1}{c\rho} \int_X \int_0^t \Phi(x - x', t - t') A(x') p(t') dt' dx'$$

We exploit the separability of Q to accelerate calculation of temperatures at specific times by calculating a time-independent Green's function given the power profile for the illuminator:

$$u(x, t_0) = \frac{1}{c\rho} \int_X \int_0^{t_0} (4\pi\alpha(t_0 - t'))^{-3/2} \exp\left(\frac{-|x - x'|^2}{4\alpha(t_0 - t')}\right) A(x') p(t') dt' \delta x'$$

$$= \frac{1}{c\rho} \int_X A(x') \int_0^{t_0} (4\pi\alpha(t_0 - t'))^{-3/2} \exp\left(\frac{-|x' - x|^2}{4\alpha(t_0 - t')}\right) p(t') dt' dx'$$

$$= \frac{1}{c\rho} \int_X A(x') G_{p(t)}(x' - x) dx'$$

for a temperature evaluated at $t_0$.

For transient analysis we provide the thermal heat density due to light source: Q=A(x)p(t) from the optical simulation to the ANSIS Fluent software and computes the time dependent heat variation by solving the equation $$c\rho \frac{\partial u}{\partial t} = \nabla_x \cdot k \nabla_x u + Q$$

using the software.

Power Analysis

The primary measurement of a laser's hazard potential to skin in laser safety calculations is the Maximum Permissible Exposure (MPE). This is the maximum irradiance or radiant exposure that may be incident upon the tissue without causing biological damage. According to the American National Standard for the Safe Use of Lasers (ANSI Z136.1) there are three rules that limit the MPE per pulse for a train of laser pulses (American National Standard for the Safe Use of Lasers). For the purpose of evaluating exposure to the skin only the first two rules are considered:
1. The MPE/pulse is limited to the MPE for any single pulse (single pulse limit).
2. The MPE/pulse is limited to the MPE for all exposure times, divided by the number of pulses n during that time period (average power limit).
3. The MPE/pulse is limited to the MPE for a single pulse multiplied by $n^{0.25}$, where n is the number of pulses that occur during the period of exposure (repetitive pulse limit).

To determine the Minimum Source Power (MSP for activation of axons in a fascicle, we chose wavelength 550 nm as the reference frequency. The MPE for a single pulse laser exposure at 550 nm can be calculated as (American National Standard for the Safe Use of Lasers):

$$MPE = 1.1 t^{0.25} \text{ J/cm}^2$$

To express this in terms of irradiance, we divide the result by the exposure cycle time (T) to obtain (note this is for our application):

$$MPE = \frac{1.1 t^{0.25}}{T} \text{ W/cm}^2$$

Assuming a train of pulses with the pulse repetition frequency of 40 Hz, an exposure time of 200 ms (e.g. 8 pulses), and pulse duration of 5 ms (this can deliver meaningful stimulation in most peripheral nerves), we arrived at the MPE limits in Table 3. These parameters have been chosen to model the effective limits of optogenetic stimulation using currently available opsins. Future increases in activation efficiency may enable changes in the design tradespace, e.g. the PRF may be able to extend to 100 Hz or higher.

TABLE 3

| MPE Rules | W/cm$^2$ | mW/mm$^2$ |
|---|---|---|
| Single pulse limit | 0.29 | 2.9 |
| Average pulse limit | 0.092 | 0.92 |

The smallest value from the two rules, 0.92 mW/mm$^2$, establishes the safe limit for maximum power exposure to the 550 nm light at a pulse repetition frequency of 40 Hz and assuming a 200 ms exposure time and 1 s cycle time.

To evaluate the degree of attenuation of light propagation inside a fascicle, we compute the attenuation factor, which is measured as the ratio between peak fluence rates of the entire cube versus the minimum fluence rate inside the fascicle. Table 4 summarizes the attenuation factor computed over multiple fascicle and illuminator geometries. The minimum value is used since it is assumed that one would like to activate every axon in the fascicle.

TABLE 4

| Attenuation Factor. | | | |
|---|---|---|---|
| | One-side light source | Four-sides light source | |
| Fascicle of diameter D = 800 μm | 0.04 | 0.647 | |
| | T = 100 μm | T = 200 μm | T = 400 μm |
| Fascicle plate of thickness T | 0.201 | 0.164 | 0.095 |

Assuming that the power required to activate genetically-sensitized axons is 0.01 W/cm$^2$, based on the attenuation factor, we can compute the minimum source power needed as:

$$E_{min} = \frac{0.01}{\alpha} \text{ W/cm}^2$$

Where α is the attenuation factor. Table 5 summarizes the minimum source power required to activate all axons within a fascicle given different illumination and fascicle geometries.

TABLE 5

| Minimum source power required to activate deepest axons within a fascicle. | | | |
|---|---|---|---|
| | One-side light source | Four-sides light source | |
| Fascicle of diameter D = 800 μm | 0.25 W/cm$^2$ | 0.02 W/cm$^2$ | |
| | T = 100 μm | T = 200 μm | T = 400 μm |
| Fascicle plate of thickness T | 0.05 W/cm$^2$ | 0.06 W/cm$^2$ | 0.11 W/cm$^2$ |

The results show that given a fascicle plate of 200 μm thickness one can activate every axon with a power of 0.06

W/cm² (0.6 mW/mm²). Comparing this first order model of fluence of light transport inside the fascicle and the MPE limit from above suggests that tissue scattering/absorption results in an order of magnitude loss in photons reaching the deepest axons. For large fascicles of circular cross-section, the minimum power required to activate the axons in the center of the fascicle exceeds the ANSI safety limit. If the cross section of the nerve is remodeled such that the resulting thickness is <0.5 mm, then optical sources on each side are only required to penetrate 250 mm of tissue to reach the center of the fascicle. The minimum source power at this thickness is ~0.72 mW/mm² which is within the maximal permissible bounds for high frequency stimulation.

We analyzed both the transient and steady state temperature rise for the fascicle as a function of various geometry and irradiation combinations. Using a simulated power density of 1 mW/mm2 we found that the steady state increase in temperature within a nerve is <0.1 degree Celsius for all configurations that were tested including unflattened fascicles <800 μm in diameter and flattened fascicles ranging in thickness from 100-400 μm. This assumed a 200 ms cycle-on time and 800 ms cycle-off time. Transient increases in temperature during cycle-on times never exceeded 0.01 degrees Celsius.

Figure 2A:
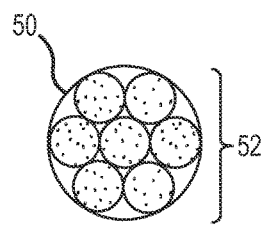
FIGS. 2a and 2b are diagrams showing a cuffed peripheral nerve bundle in its initial and reshaped states.
Figure 2B:
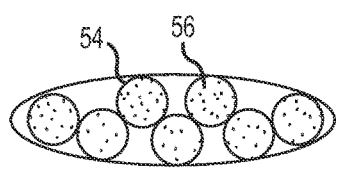

Referring now to FIGS. 2a and 2b, a cuff 50 is placed around a peripheral nerve bundle 52 and used to reshape the nerve bundle to about one-half its original height. As described in U.S. Pat. No. 6,456,866, the change in height is limited to about 2× due to the increase in pressure in the blood vessels around the nerves. The primary effect of the reshaping is to reorganize the fascicles 54 into approximately a single layer. The cuff does not reshape the individual fascicles or reorganize the axons 56 within the fascicle. A peripheral nerve bundle 52 may have a diameter of 1.5 to 3 mm. Reshaping reduces the thickness of the nerve bundle to approximately 0.75 mm to 1.5 mm. However, reshaping does not flatten the individual fascicles.

Figure 3A:
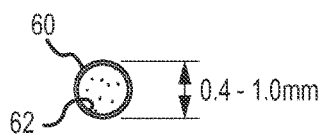
FIGS. 3a and 3b are diagrams showing a cuffed single fascicle in its initial and reshaped states.
Figure 3B:
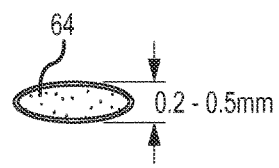

Referring now to FIGS. 3a and 3b, a cuff 60 is placed around a single fascicle 62 and used to reshape the fascicle to about one-half its original height. The primary effect of the reshaping is to reorganize the axons 64 into a thinner layer without reshaping (and damaging) the axons. Individual fascicles have a diameter of 0.4 to 1 mm. Reshaping reduces the thickness of the fascicle to approximately 0.2 mm to 0.5 mm. Flattening of the single fascicle to less than 0.5 mm is critical to satisfying the MPE limitations as well as exploiting the inherent spatial resolution advantages of the optical sources.

Figure 4A:
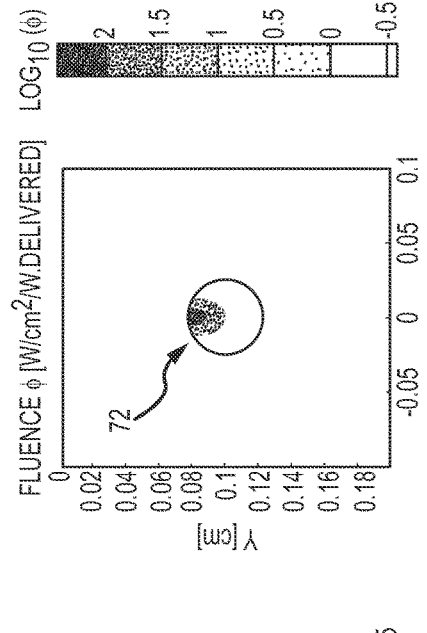
FIGS. 4a, 4b and 4c are plots of fluence over the cross-section of the nerve derived from detailed computer simulations of light scattering in nerves for a peripheral nerve bundle, a single fascicle and a single reshaped fascicle, respectively.
Figure 4B:
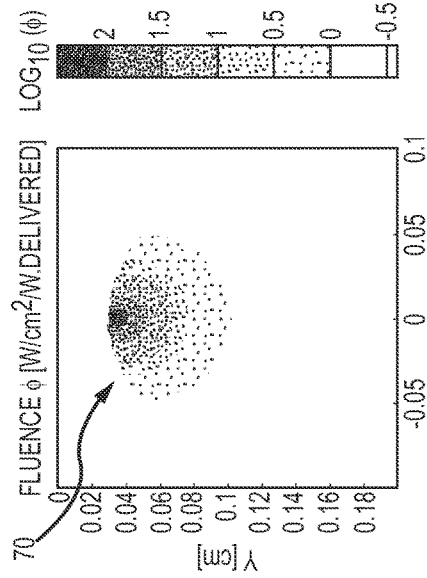
Figure 4C:
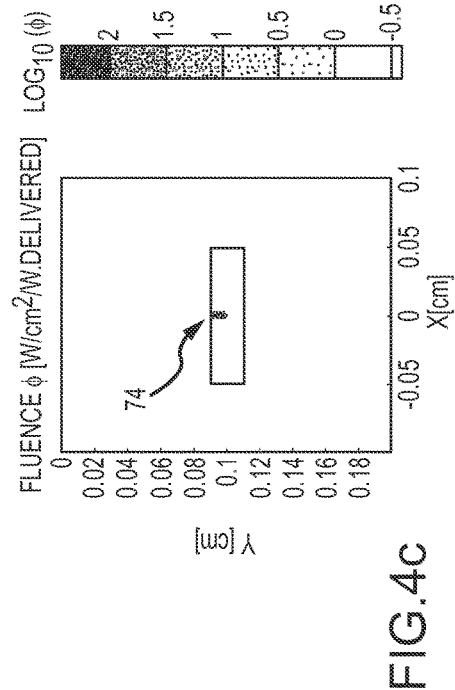

Referring now to FIGS. 4a, 4b and 4c, we simulated the specific attenuation at the center of the Macaque median nerve (a peripheral nerve bundle with a 1.5 mm diameter), a 0.5 mm diameter fascicle and the same fascicle reshaped into an axon layer with a thickness of 0.2 mm and plotted the relative fluence for the nerve. For each plot, we set the LED power so that a single LED can excite an axon at the center of the fiber bundle or fascicle having an activation threshold of 20 mW/cm². Fluence power inside the nerve that is less than the activation threshold is masked out for clarity. 20 mW/cm2 represents a very conservative activation threshold (hardest to activate) among today's existing opsins. Note that these parameters have been chosen to model the effective limits of optogenetic stimulation using currently available opsins. Future increases in activation efficiency may enable changes in the design tradespace (e.g. maximum stimulation frequency, maximum thickness of fascicles).

As shown in the plot of fluence 70 in FIG. 4a for the peripheral nerve bundle, it requires 282 μW to activate the axon at the center of the nerve. The surface power density is 282 μW/(50 μm)²=113 mW/mm²—well over the safe limit for biological tissue (2.9 mW/mm²). Furthermore, a very large number of axons are activated over 33.1% of the nerve cross-section. In order for an optogenetic approach to be successful, we must remodel the structure of the nerve to decrease the impact of attenuation and scattering.

As shown in the plot of fluence 72 in FIG. 4b for a single unremodeled fascicle, it requires 21.4 μW to activate the axon at the center of the nerve. The surface power density is ~8.6 mW/mm² which still exceeds the safe limit for biological tissue (again assuming a source that is 50×50 μm). However, the single LED still activates 26.7% of the fascicle cross-section.

As shown in the plot of fluence 74 in FIG. 4c for a single reshaped fascicle, it requires only 2.3 μW to activate the axon at the center of the nerve. The surface power density is 0.92 mW/mm2—well within the safe limit for biological tissue for low frequency stimulation and just inside our bound for higher frequency stimulation. The surface fluence is reduced by 120X relative to the surface fluence required to stimulate the central axon in an un-modified median nerve. Furthermore, a single LED activates only 2.5% of the fascicle cross-section.

The modeling and simulations indicate that all axons in a single reshaped fascicle with a height between 0.2 and 0.5 mm can be active using an input power density of less than 1 mW/mm². In all cases, the increase in tissue temperature from irradiation was 0.1 C or less, well within the 2 C requirement.

In order to reshape a fascicle to a height between 0.2 and 0.5 the cuff component of the FOCI must be configured for a single nerve fascicle having an external configuration with a height Y and a width X. Typical fascicles have a diameter (height) of between 0.4 and 1.0 mm. The cuff comprises an optically transparent elastic collar member defining an internal opening which has an internal configuration having a height less than Y and between 0.2 mm and 0.5 mm and a width greater than X. The collar member includes a material that exerts a force on the nerve fascicle that will cause the fascicle to gradually reshape to the internal configuration of said opening. The gradual reshaping of the fascicle reorganizing the axons within the fascicle without reshaping the individual axons. The cuff design may be modeled after the FINE or SC-FINE designs but dimensioned to accept a single fascicle of at most 1 mm in diameter and to reshape the fascicle to a height of 0.5 mm or less.

Figure 5B:
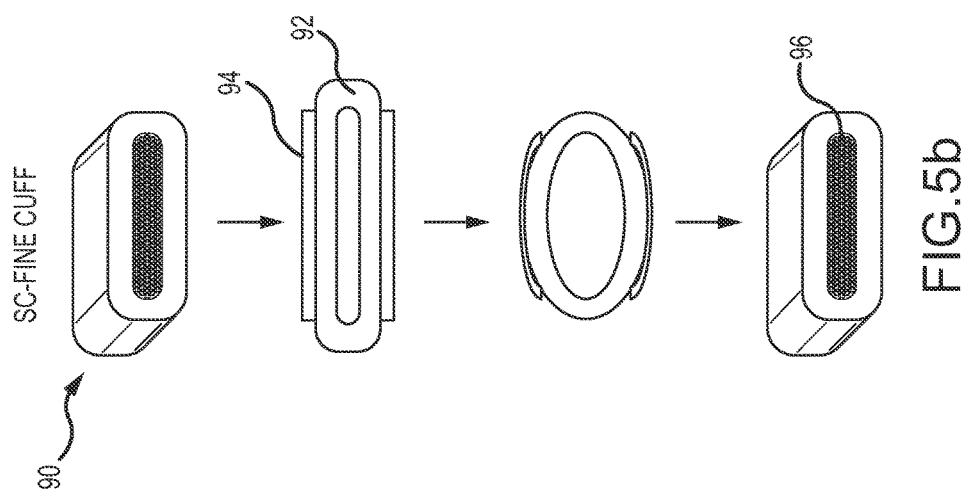
FIGS. 5a and 5b are diagrams of alternate embodiments of the cuff for reshaping a single fascicle.
Figure 5A:
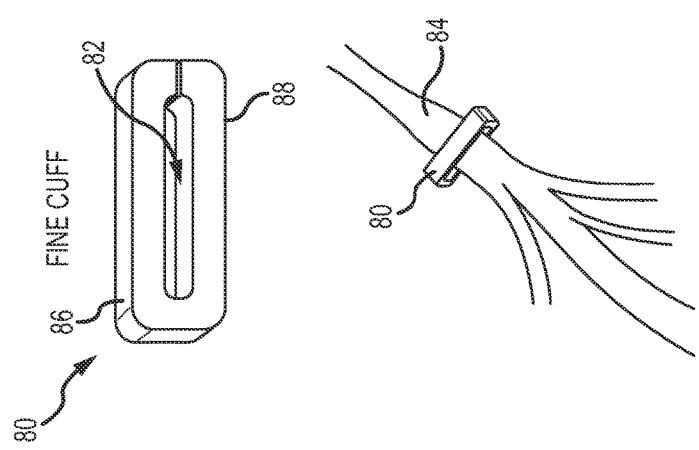

As shown in FIG. 5a, a cuff 80 based on the FINE configuration includes an elongated, substantially rectangular central opening 82 having a height, which is smaller than and a width which is longer than the diameter of the nerve 84 to which it is applied. The interior of the cuff is micro-textured through the molding process to grip the epineurium/perineurium. The cuff may be made of a material having a sufficient elasticity and a shape sufficient to cause a force applied selectively across the transverse direction of the nerve. The nerve cuff can be open at a single end or alternatively the nerve cuff may be open at two ends. The open ends are closed such as by staple, an O-ring in a grooved area, a suture, a mechanical interference fit or other closure mechanism. The top and bottom beams 86 and 88 which form the top and/or bottom of the nerve cuff and the connecting juncture for these beams have a structure and/or material characteristic tailored to impart a particular pressure to the nerve to gradually reshape the nerve to the integral configuration of central opening 82.

As shown in FIG. 5b, a cuff 90 based on the SC-FINE configuration comprises a molded silicone rubber (MED-4870, Nusil) collar member 92 coated with a biodegradable copolymer, poly DL lactic-co-glycolic acid (PLGA, Sigma) film 94. The copolymer film 94 keeps the collar member 92 open until implantation, and following implantation, as the PLGA degrades into bio-safe hydroxy acids, the cuff slowly returns to its rest dimensions of an internal opening 96, thereby reshaping the nerve and fascicle. The interior of the cuff will be microtextured through the molding process to grip the epineurium/perineurium.

Configuring the elastic cuff for a single fascicle to have a reshaped cross-section that is both relatively flat and has a height between 0.2 and 0.5 mm addresses the power limitations and the spatial resolution for an optical source. However, the optical interface component of the FOCI must be configured to effectively stimulate axons over the entire cross-section of the reshaped nerve fascicle along a length of the nerve of at least 2 mm. The nerve and FOCI may be configured for single or multi-wavelength stimulation (uni-directional) or single or multi-wavelength stimulation and recording (bi-directional). Once implanted, the optical interface will require calibration to map the array of optical sources to their corresponding target nerves and their neurophysiological response to stimulation.

A challenge unique to optogenetics is that nerves are coated with myelin, which is an insulating sheath that limits the ability to electrically stimulate at those locations. The myelin is organized such that each sheath extends ~1.5-2 mm down the length of the nerve before the nerve membrane is exposed for a very short distance (~50 um) followed by another segment of myelin. These gaps are called "Nodes of Ranvier" and they are the only access points for optically stimulating the nerve. Every axon in the nerve will have at least one Node of Ranvier in 2 mm of length. Configuring the optical interface to stimulate axons along a length of at least 2 mm guarantees access to a Node of Ranvier for each axon. The cuff in practice must be bigger than that to accommodate the electrode contacts etc.

Referring now to FIGS. 6a and 6b, an embodiment of an optical interface 100 for a FOCI comprises a plurality of optical sources 102 (e.g., LEDs) arranged in two-dimensional arrays 103 on opposing sides of a cuff 104 about a single fascicle 106. The fascicle has a plurality of peripheral nerve axons 108, each having Nodes of Ranvier 110 that are staggered and repeat about every 2 mm. In this embodiment, optical sources 102 are configured to emit pulsed light 112 in non-overlapping fields-of-view (FOV) 114 within the volume of the reshaped fascicle 106 e.g., along the length of an axon 108 or the width of a fascicle-cross section 116. The light is effectively collimated over the short distance. Depending on the divergence characteristics of the source, a collimating lens may or may not be required. The advantage of collimated light is power efficiency and reduced exposure of the tissue.

If the FOCI is configured to stimulate a single functional modality or sub-modality of the nerve, all of the optical sources 102 are configured to emit at the same fixed-wavelength corresponding to the genetic modification of the nerve e.g. 550 nm. In this configuration, a high percentage of the optical sources will not stimulate an axon, either the axons they irradiate have not been genetically modified or the radiated location of a genetically modified axon does not correspond to a Node of Ranvier. During calibration, a "mapping" of the optical sources that do stimulate the genetically modified axons may be determined and used to configure the optical sources to both save power and avoid unnecessary irradiance of the nerve. Conversely, by selecting LEDs having a footprint of approximately 50 microns×50 microns and forming arrays at least 2 mm in length, the optical interface can access and stimulate at least one Node of Ranvier for each genetically modified axon in the fascicle.

If the FOCI is configured to stimulate multiple functional sub-modalities of the nerve, different subsets of the optical sources 102 are configured to emit at different wavelengths corresponding to the different genetic modifications of the nerve e.g. 410 nm, 500 nm and 625 nm. If the optical sources are fixed wavelength there is no guarantee that each Node of Ranvier of a genetically modified access will be irradiated with the correct wavelength of light and stimulated. However, a typical fascicle may have 10,000 to 100,000 individual axons. As such there is considerable redundancy and overlapping receptive fields among the axons for a particular sub-modality. Statistically some percentage of those axons will be stimulated. During calibration, a "mapping" of the optical sources that do stimulate the genetically modified axons may be determined and used to configure the optical sources to both save power and avoid unnecessary irradiance of the nerve.

If the optical sources have a selectable wavelength, during calibration a "mapping" can be determined to identify both the location and wavelength of the sources that address each Node of Ranvier. The wavelength may be "selectable" by physically configuring fixed wavelength sources of the particular wavelength for each mapping. This tailors the optical interface for each FOCI to a particular fascicle. The wavelength may also be "selectable" by providing an optical source that is directly tunable to, for example, one of three possible defined wavelengths or providing a filter that is tunable to one of the three wavelengths.

Referring now to FIGS. 7a and 7b, an embodiment of an optical interface 200 for a FOCI comprises a plurality of optical sources 202 (e.g., LEDs) arranged in two-dimensional arrays 203 on opposing sides of a cuff 204 about a single fascicle 206. The fascicle has a plurality of peripheral nerve axons 208, each having Nodes of Ranvier 210 that are staggered and repeat about every 2 mm. In this embodiment, optical sources 202 are configured to emit pulsed light 212 in overlapping fields-of-view (FOV) 214 within the volume of the reshaped fascicle 206. The light is effectively uncollimated over the short distance. Depending on the divergence characteristics of the source, a diverging lens may or may not be required.

Although this configuration can be used with single-wavelength sources or multi-wavelength tunable sources it may be particularly useful for a multi-wavelength, fixed-wavelength optical source configuration. Staggering the different color optical sources and overlapping their FOV 214 increases the likelihood that a given Node of Ranvier will be stimulated by the correct wavelength source. During calibration, if two or three different sources each illuminate a Node of Ranvier, the correct source can be identified and mapped and the remaining sources deactivated. The tradeoff for using overlapping FOV or "uncollimated" light is reduced power efficiency and increased exposure of the issue.

Referring now to FIGS. 8a, 8b and 8c, a FOCI 300 includes an elastic cuff 302, an optical interface 304 and an electrical interface 306. Electrical interface 306 includes at least one row of sensing electrodes 308 that span the width of cuff 302 and are in contact with the surface of the tissue. Optical interface 304 is configured to stimulate genetically modified axons in the fascicle. Electrical interface 304 is configured to sense and record the activity of axons in the fascicle, either the activity of the optically stimulated axons themselves or the activity of other axons in response to that optical stimulation (e.g. activity of motor nerves in response to sensory activation). There is no cross-talk between the optical stimulation and the electrical sensing and recording.

In an embodiment, microelectronics 310 controls the optical interface 304 to emit pulsed light at a certain power level to stimulate the axons. This stimulation produces electrical nerve firing. Electrical interface 306 senses and records the level of electrical nerve firing. A feedback element 312 is configured to feedback the electrical activity to the microelectronics 310 to control the emission of pulsed light from the optical sources to calibrate the stimulative effect on the axons. This may be a gross calibration to set the overall gain level to get a desired average effect. This may be a fine calibration of individual sources or small subsets of sources to set a local scale factor for a particular axon and Node of Ranvier. The amount of power required to stimulate a Node can vary based on the depth of the axon in the cross-section of the fascicle. This can be done at the initial calibration of the implant, and possibly periodically to maintain calibration.

In another embodiment, electrical interface 306 senses and records the level of electrical nerve firing from axons of a different modality. For example, the optical interface 304 may stimulate sensory nerves and the electrical interface 306 may sense and record motor nerve activation. The feedback element 308 may for example feedback the motor nerve response to a prosthetic 314 to control motor function.

In another embodiment, the electrical interface 306 is configured to provide both closed-loop feedback for the stimulated axons and recording of nerve firing from axons of a different modality. The electrical interface 306 controls the activation of the optical sources, hence timing of the optical stimulation, and therefore can discriminate whether the sensed electrical activity is likely to correspond to the stimulated axons or to another modality.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A flat optogenetic cuff interface (FOCI) for functional optical stimulation of axons in a single fascicle of a human peripheral nerve, wherein said axons have been genetically modified to express light sensitive proteins for excitation or inhibition of the nerves, said system comprising:
   a cuff configured for a single human nerve fascicle having an external configuration with a cross-section height Y and a cross-section width X, the cuff comprising an elastic collar member defining an internal opening which has an internal configuration having an initial cross-section height between 0.4 mm and 1.0 mm and a reshaped cross-section height between 0.2 mm and 0.5 mm and a width greater than X, said collar member including a material that exerts a force on said nerve fascicle that will cause the fascicle to gradually reshape to the internal configuration of said opening with a cross-section height between 0.2 mm and 0.5 mm with a change in cross-section height limited to a maximum of 2x, said gradual reshaping of the fascicle reorganizing the axons within the fascicle without reshaping the individual axons;
   an optical interface comprising a plurality of optical sources arranged in two-dimensional arrays on opposing sides of the cuff, each said optical source configured to illuminate a length of the nerve of at least 50 microns and less than 10% of the cross-section of the reshaped nerve fascicle, said optical sources configured to emit pulsed light at a pulse repetition frequency (PRF) to penetrate the reshaped nerve fascicle from opposing sides at a power level such that the irradiance incident upon tissue at the PRF throughout the reshaped nerve fascicle is less than a Maximum Permissible Exposure (MPE) to selectively irradiate and stimulate all of the axons in the single fascicle over an entire cross-section of the reshaped nerve fascicle along a length of the nerve of at least 2 mm at a level greater than a Minimum Source Power (MSP) to stimulate axons; and
   an electrical interface comprising a plurality of electrodes across the width of the cuff configured to sense activity of axons within the fascicle.

2. The FOCI of claim 1, wherein the optical sources emit pulsed light at the same wavelength.

3. The FOCI of claim 1, wherein axons with different functional modalities are genetically modified to express light sensitive proteins for excitation or inhibition of the nerves at different wavelengths, wherein different subsets of the optical sources emit pulsed light at the different wavelengths.

4. The FOCI of claim 3, wherein the optical sources emit pulsed light in non-overlapping fields of view (FOV) within the reshaped fascicle.

5. The FOCI of claim 4, wherein the optical sources in each subset emit pulsed light at a fixed wavelength.

6. The FOCI of claim 4, wherein the optical sources emit pulsed light at selectable wavelengths, wherein the two-dimensional array of optical sources is configured according to a mapping of the Nodes of Ranvier for the different functional modalities.

7. The FOCI of claim 3, wherein the optical sources in different subsets are staggered within the two-dimensional array to emit pulsed light at different wavelengths in overlapping fields of view (FOV) within the reshaped fascicle.

8. The FOCI of claim 1, wherein the said collar member has a top beam and a bottom beam formed of a silicone elastomer.

9. The FOCI of claim 1, wherein the elastic collar member is optically transparent, wherein the optical interface and electrical interface are embedded within the optically transparent elastic collar member.

10. The FOCI of claim 9, wherein said collar member comprises a silicone elastomer having an original geometry that defines the internal configuration of the internal opening with a height between 0.2 and 0.5 mm, further comprising a biodegradable co-polymer film bonded onto a stretched collar member having a geometry with at least height Y and width X that fits the single nerve fascicle, wherein over time the co-polymer film degrades in-situ and the collar member relaxes back to its original geometry causing the fascicle to gradually reshape to the internal configuration of the opening.

11. A method for functional optical stimulation of axons in a single fascicle of a human peripheral, wherein said axons have been genetically modified to express light sensitive proteins for excitation or inhibition of the nerves, said method comprising:
   placing a flat optogenetic cuff interface (FOCI) around a single human nerve fascicle, said single nerve fascicle having an external configuration with a cross-section height Y and a cross-section width X, the cuff comprising an elastic collar member defining an internal opening which has an internal configuration having an initial cross-section height between 0.4 mm and 1.0 mm and a reshaped cross-section height between 0.2 mm and 0.5 mm and a width greater than X, said collar member including a material that exerts a force on said nerve fascicle that will cause the fascicle to gradually reshape to the internal configuration of said opening with a cross-section height between 0.2 mm and 0.5 mm, said cuff further comprising an optical interface comprising a plurality of optical sources arranged in two-dimensional arrays on opposing sides of the cuff, each said optical source configured to illuminate a length of the nerve of at least 50 microns and less than 10% of the cross-section of the reshaped nerve fascicle, said optical sources configured to emit pulsed light at a pulse repetition frequency (PRF) and an electrical interface comprising a plurality of electrodes across the width of the cuff configured to sense activity of axons within the fascicle;

applying a gradual force to the single fascicle by means of the cuff to gradually reshape the fascicle by reorganizing the axons within the fascicle without reshaping the individual axons such that the reshaped fascicle has a height between 0.2 mm and 0.5 mm with a change in cross-section height limited to a maximum of 2×;

activating the optical sources to emit pulsed light to penetrate the reshaped nerve fascicle from opposing sides at a power level such that the irradiance incident upon tissue at the PRF throughout the reshaped nerve fascicle is less than a Maximum Permissible Exposure (MPE) to selectively irradiate and stimulate all of the axons in the single fascicle over an entire cross-section of the reshaped nerve fascicle along a length of the nerve of at least 2 mm at a level greater than a Minimum Source Power (MSP) to stimulate axons; and sensing via the electrical interface activity of the stimulated axons.

12. The method of claim 11, wherein the elastic collar member is optically transparent, wherein the optical interface and electrical interface are embedded within the optically transparent elastic collar member.

13. The method of claim 12, wherein said elastic collar member comprises a silicone elastomer having an original geometry that defines the internal configuration of the internal opening with a height between 0.2 and 0.5 mm, further comprising a biodegradable co-polymer film bonded onto a stretched collar member having a geometry with at least height Y and width X that fits the single nerve fascicle, wherein over time the co-polymer film degrades in-situ and the collar member relaxes back to its original geometry causing the fascicle to gradually reshape to the internal configuration of the opening.

14. The method of claim 11, wherein axons with different functional modalities are genetically modified to express light sensitive proteins for excitation or inhibition of the nerves at different wavelengths, wherein different subsets of the optical sources emit pulsed light at the different wavelengths.

* * * * *